(12) United States Patent
Cyphert et al.

(10) Patent No.: US 9,538,788 B2
(45) Date of Patent: Jan. 10, 2017

(54) ELECTRONIC CIGARETTE

(71) Applicant: Vapor Corp., Dania Beach, FL (US)

(72) Inventors: Gilbert Cyphert, Phoenix, AZ (US); Xuandong Huang, Sichuan (CN); Edwin Balder, Mesa, AZ (US)

(73) Assignee: VAPOR CORP., Dania Beach, FL (US)

( * ) Notice: Subject to any disclaimer, the term of this patent is extended or adjusted under 35 U.S.C. 154(b) by 112 days.

(21) Appl. No.: 13/999,652

(22) Filed: Mar. 14, 2014

(65) Prior Publication Data
US 2015/0047658 A1 Feb. 19, 2015

Related U.S. Application Data

(60) Provisional application No. 61/852,336, filed on Mar. 15, 2013.

(51) Int. Cl.
*A24F 47/00* (2006.01)
(52) U.S. Cl.
CPC .................................. *A24F 47/008* (2013.01)
(58) Field of Classification Search
CPC ..................................................... A24F 47/008
See application file for complete search history.

(56) References Cited

U.S. PATENT DOCUMENTS

| | | | | |
|---|---|---|---|---|
| 4,074,111 A | * | 2/1978 | Hunter | A61L 9/03 |
| | | | | 392/393 |
| 4,508,991 A | * | 4/1985 | Wurster | H01K 1/32 |
| | | | | 313/579 |
| 7,832,410 B2 | | 11/2010 | Hon | |
| 2011/0265806 A1 | * | 11/2011 | Alarcon | A24F 47/00 |
| | | | | 131/273 |
| 2013/0042865 A1 | * | 2/2013 | Monsees | A61M 15/06 |
| | | | | 128/203.27 |
| 2013/0192620 A1 | * | 8/2013 | Tucker | H01C 17/00 |
| | | | | 131/329 |
| 2013/0247924 A1 | * | 9/2013 | Scatterday | A61M 15/06 |
| | | | | 131/329 |
| 2013/0298905 A1 | * | 11/2013 | Levin | A24F 47/008 |
| | | | | 128/202.21 |
| 2014/0000638 A1 | * | 1/2014 | Sebastian | A24F 47/008 |
| | | | | 131/328 |

FOREIGN PATENT DOCUMENTS

CN 102423145 4/2012

* cited by examiner

*Primary Examiner* — Michael H Wilson
*Assistant Examiner* — Eric Yaary
(74) *Attorney, Agent, or Firm* — Geoffrey A. Lottenberg

(57) ABSTRACT

An electronic cigarette is provided. The electronic cigarette includes a casing having two chambers located sequentially within the casing. A battery and a fluid are located in the casing. A sealing element forms a partition between the chambers. A tube element is located in the second chamber, providing an air passage between the two chambers. Also included is a fiber element that transfers fluid from a fluid containing member to a heating assembly.

13 Claims, 9 Drawing Sheets

ELECTRONIC CIGARETTE

Priority is claimed to provisional patent application Ser. No. 61/852,336, filed Mar. 15, 2013, entitled: "Electronic Cigarette," which is referred to and incorporated herein in its entirety by this reference.

FIELD OF THE INVENTION

The present invention relates to an electronic cigarette, in particular to an electronic cigarette that contains only nicotine without tar.

BACKGROUND OF THE INVENTION

Despite the fact that "smoking is harmful to your health", the number of smokers worldwide is up to 1 billion, and the number is increasing every year. In 2003, the World Health Organization (WHO) concluded a global Framework Convention on Tobacco Control. According to the statistical data from WHO, about 4.9 million people die of diseases caused by smoking each year. Although smoking may cause serious respiratory diseases and cancer, it remains extremely difficult for smokers to quit smoking.

The active ingredient in a cigarette is nicotine. During smoking, nicotine, along with tar aerosol droplets produced in the cigarette when it burns, enters a smoker's alveolus and is rapidly absorbed. After being absorbed into the blood of a smoker, nicotine then produces its effect on the receptors of the smoker's central nervous system, which makes the smoker relax and enjoy an inebriety similar to that produced by an exhilarant.

Nicotine is a kind of alkaloid with a low molecular weight and its half-life in blood is quite short. The major harmful substance in tobacco is tar, which is composed of thousands of ingredients, tens of which are carcinogenic substances. It has been proven that passive smoking can be more harmful to non-smokers than smoking is to the smoker.

Some cigarette substitutes containing only nicotine without tar have been proposed, many of them, such as the "nicotine patch," "nicotine mouthwash," "nicotine chewing gum," "nicotine drinks" etc., are made of pure nicotine. Although these cigarette substitutes are free from tar, their major disadvantage is that an effective peak concentration of nicotine cannot be reached in the blood of a smoker due to slow absorption of the nicotine. In addition, these cigarette substitutes cannot satisfy the habitual smoking actions of a smoker, for example, the inhaling action and the physical manipulation of the cigarette itself.

Therefore, there remains a need to overcome one or more of the limitations in the above-described, existing art. The discussion of the background to the invention included herein is included to explain the context of the invention. This is not to be taken as an admission that any of the material referred to was published, known, or part of the common general knowledge at the priority date of the claims.

It will be recognized that some or all of the Figures are schematic representations for purposes of illustration and do not necessarily depict the actual relative sizes or locations of the elements shown. The Figures are provided for the purpose of illustrating one or more embodiments of the invention with the explicit understanding that they will not be used to limit the scope or the meaning of the claims.

DETAILED DESCRIPTION OF THE PREFERRED EMBODIMENTS

In the following description, for the purposes of explanation, numerous specific details are set forth in order to provide a thorough understanding of the electronic cigarette of the present invention. It will be apparent, however, to one skilled in the art that the electronic cigarette may be practiced without some of these specific details. Throughout this description, the embodiments and examples shown should be considered as exemplars, rather than as limitations on the electronic cigarette. That is, the following description provides examples, and the accompanying drawings show various examples for the purposes of illustration. However, these examples should not be construed in a limiting sense as they are merely intended to provide examples of the electronic cigarette rather than to provide an exhaustive list of all possible implementations of the electronic cigarette.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

Figure 1:
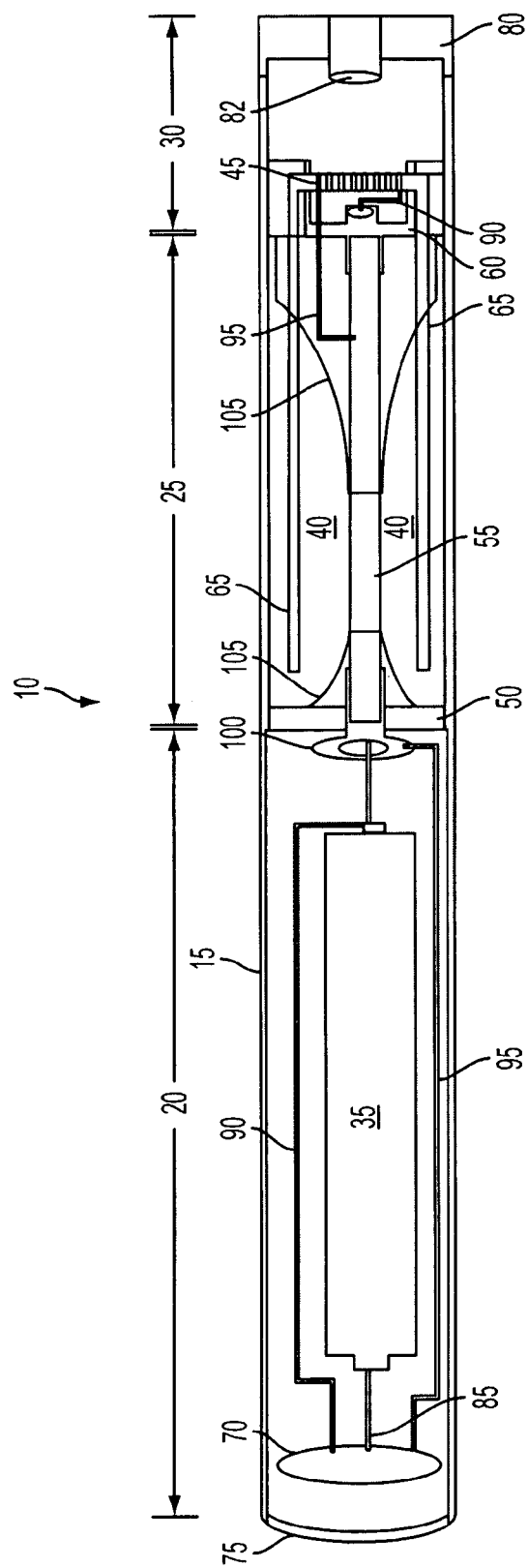
FIG. 1 is a cross-sectional view of one embodiment of an electronic cigarette embodying the principals of the invention.

Referring to FIG. 1, an electronic cigarette 10 is illustrated. As shown in FIG. 1, the electronic cigarette 10 comprises a cylindrical casing, or tube 15 that may be constructed of stainless steel, plastic, or other materials. Within the cylindrical casing 15, a first chamber 20, a second chamber 25, and a third chamber 30 are formed, the three chambers located sequentially within the cylindrical casing 15.

A battery 35 is located in the first chamber 20, a liquid, or fluid 40 is located in the second chamber 25, and a heating element 45 is located in the third chamber 30. In one embodiment, the liquid 40 contained in the electronic cigarette 10 comprises: glycol, nicotine, water based flavors of regular or menthol (or other desired flavors). The heating element 45 may be made of platinum wire, nickel chromium alloy or iron chromium aluminum alloy wire with a rare earth element. The battery 35 may be lithium, but other materials and types of batteries may be employed, including disposable types.

A first seal 50 forms a partition between the first 20 and second 25 chambers. The first seal 50 may be constructed of rubber, silicone, plastic or other materials. The first seal includes a hole or aperture in which a portion of a tube 55 is located. The tube 55 extends substantially the length of the second chamber 25 allowing passage of air from the first chamber 20 into the third chamber 30.

A second seal 60 forms a partition between the second 25 and third 30 chambers. In one embodiment, the second seal 60 comprises a ceramic material shaped substantially in a "T." The "leg" of the "T" comprises a hollow cylinder that receives one end of the tube 55 and the "top" of the "T" comprises two arms that form the seal between the second 25 and third 30 chambers, and may also hold, or fix the heating element 45 in position in the third chamber 30.

The electronic cigarette 10 also includes a cotton or other fiber material 65 that has a first segment in contact with the heating element 45, and a second segment located in the second chamber 25, so that the fiber material 65 can carry or transfer the fluid 40 from the second chamber 25 to the heating element 45.

In one embodiment, the fiber material comprises a high-temperature fiberglass fabric, but other materials may be employed, such as cotton, high-temperature conduction oil cotton, or other materials. The fiber material 65 also may be positioned by the second seal 60 to aid in sealing the second chamber 25 from the third chamber 30.

An air pressure switch is located at a distal end of the first chamber 20 and may be mounted on, or separate from a printed circuit board 70. A light-emitting diode 75 (LED) is located adjacent to the printed circuit board 70, with the LED 75 forming an end-cap at one end of the electronic cigarette 10. A mouthpiece (not shown) may be located at the other end of the electronic cigarette 10, with the mouthpiece coupled to the end-cap 80 that includes a small aperture, or end-cap aperture 82 that allows passage of air from the third chamber 30 though the mouthpiece and into a user's mouth. The end-cap 80 may be made of silicone, plastic, metal or other materials.

The printed circuit board, or chip 70 includes the air pressure switch, which may be integral to the chip or may be a separate element that communicates with the chip. In one embodiment, the chip and air pressure switch comprise an electronic assembly that allows communication between the air pressure switch and the other components comprising the printed circuit board. For example, in one embodiment, the printed circuit board, or chip may comprise an embedded data processor connected via an internal bus to a read only memory containing the executable code for causing the microprocessor to perform the functions described herein. In another embodiment, the printed circuit board, or chip may comprise one or more electronic circuits that employ one or more switches to perform the functions described herein.

As shown in FIG. 1, the printed circuit board, or chip 70 has three wires coupled to it, the anode wire 85, the cathode wire 90 and the air pressure switch wire 95. The anode wire 85 runs from the printed circuit board 70 to the anode side of the battery. The cathode wire 90 connects the printed circuit board 70 to the cathode side of the battery, and then passes through the first seal 50 and into tube 55 connecting to a first end of the heating element 45 by extending all the way through the tube 55. The air pressure switch wire 95 connects the air pressure switch to the second end of the heating element 45, by also passing through the first seal 50 and then into the tube 55.

Sealing member 100 may be coupled to the tube 55 to provide additional sealing to prevent passage of fluid 40 from the second compartment 25 into the first compartment 20. The sealing member 100 may comprise a cylindrical shape at one end that receives the tube 55 and a shoulder or flange at the other end that aids in sealing the hole or aperture in the first seal 50 seal.

In addition, two sealing tubes 105 are included to seal each end of the second chamber 25. As shown in FIG. 1, one sealing tube 105 contacts the first seal 50, with the other end contacting the entire perimeter, or circumference of tube 55 so that the area where the tube 55 engages with the first seal 50 is kept free of the fluid 40. Similarly, at the other end of the second chamber 25, a second sealing tube 105 contacts the entire perimeter of tube 55 with a distal end enclosing the elements located at the end of the second chamber 25. However, the fiber material 65 extend through holes in the sealing tube 105 so that fluid 40 can pass along the fiber material 65 to the heating element 45. But, the air pressure switch wire 95, and cathode wire 90, as well as the end of the tube 55 that engages with the second seal 60 are kept free of the fluid 40. Optionally, cotton batting (not shown) may be positioned around the tube 55 and under, or within the two sealing tubes 105 to aid in sealing so that the fluid 40 does not reach either end of the tube 55, or the other areas sealed by the two sealing tubes 105.

An air inlet (not shown), in the form of a hole or aperture, may be located in the external wall of the casing 15 allowing passage of ambient air into the first chamber 20.

The printed circuit board, or chip 70 in conjunction with the air pressure switch controls the function of the electronic cigarette 10. According to one embodiment, outside, or ambient air is drawn into the first chamber 20 through the air inlet (not shown). The air pressure switch senses the low pressure formed by a user "drawing" on the mouthpiece (not shown), and activates the heating element 45 by allowing electricity to flow from the battery to the heating element 45. The LED 75 also illuminates at this time. The air flows down the tube 55 and into the third chamber 30, where the heating element 45 has atomized, or vaporized some of the fluid 40 that is carried to the heating element 45 on the fiber material 65. The vaporized fluid mixes with the air, and passes though end-cap aperture 82 that allows passage of the mixture from the third chamber 30 though the mouthpiece and into a user's mouth.

In one embodiment, the electronic cigarette 10 is disposable. During operation, if a user smokes for more than 5 seconds per puff the LED flashes two times then shuts off, or will flash ten times, which indicates the battery 35 is running low on stored power.

Figure 2:
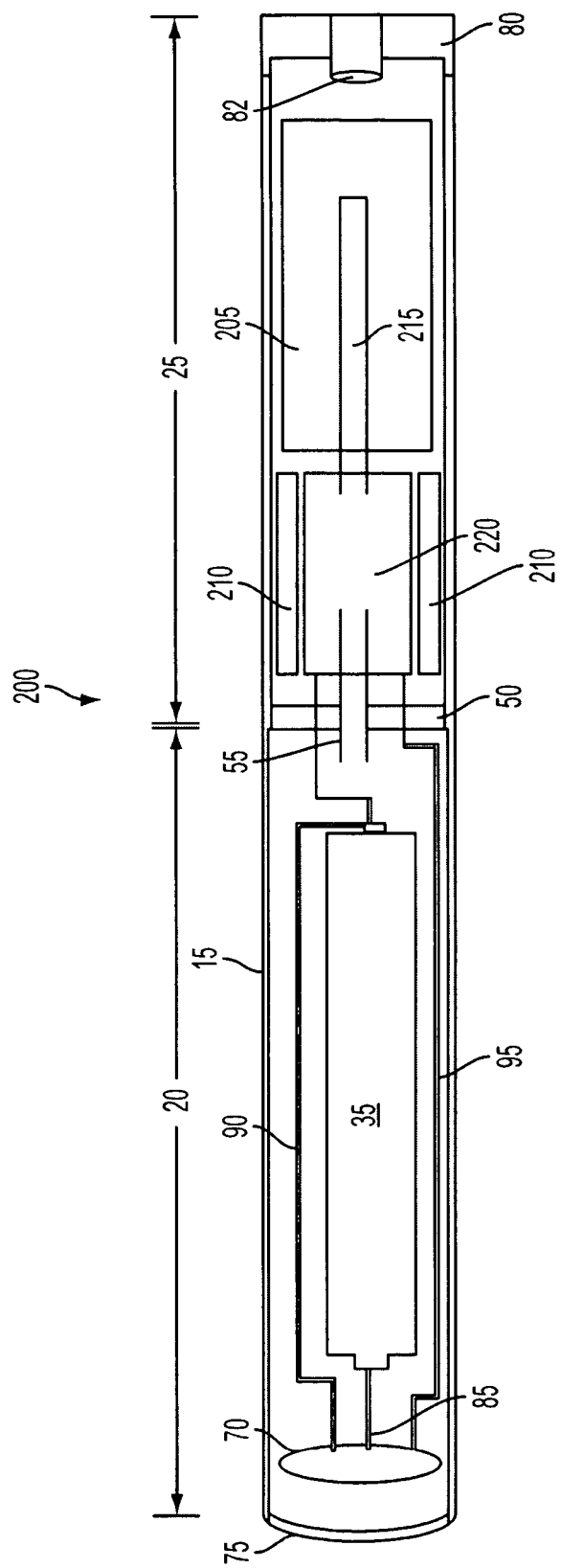
FIG. 2 is a cross-sectional view of a second embodiment of an electronic cigarette embodying the principals of the invention.

Referring to FIG. 2, another embodiment electronic cigarette 200 is illustrated. As shown in FIG. 2, the electronic cigarette 200 comprises a cylindrical casing, or tube 15 that may be constructed of stainless steel, plastic, or other materials. Within the cylindrical casing 15, is a first chamber 20 and a second chamber 25 are formed, the two chambers located within the cylindrical casing 15.

A battery 35 is located in the first chamber 20, and a fluid container 205 is located in the second chamber. The fluid container 205 contains a liquid mixture such as glycol, nicotine, water based flavors of regular or menthol (or other desired flavors). The battery 35 may be lithium, but other materials and types of batteries may be employed, including disposable types, such as AAA or AA sized batteries.

A first seal 50 forms a partition between the first 20 and second 25 chambers. The first seal 50 may be constructed of rubber, silicone, plastic or other materials. The first seal includes a hole or aperture in which a portion of a tube 55 is located. The tube 55 extends into a heating assembly 220 and allows passage of air from the first chamber 20 into the second chamber 25.

Figure 3:
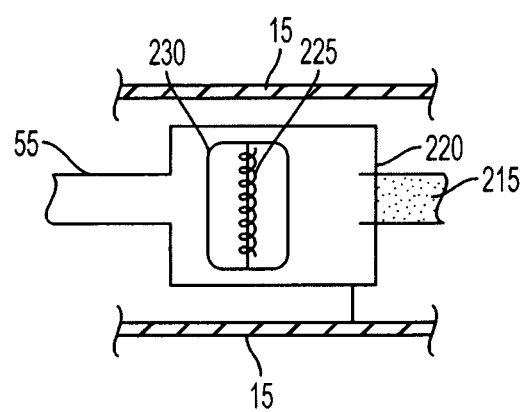
FIG. 3 is a cross-sectional view of a portion of the second embodiment of an electronic cigarette illustrated in FIG. 2.

Referring now to FIG. 3, in one embodiment, the tube 55 comprises a ceramic, brass, or other metal material shaped substantially in a "T." The "leg" of the "T" comprises a hollow cylinder that comprises one end of the tube 55 and the "top" of the "T" comprises two arms that hold, or fix a tempered glass bulb 230 in position in the heating assembly 220. Inside the tempered glass bulb 230 is a heating wire 225 that heats the glass bulb 230 that then heats the fluid that is introduced into the heating assembly 220 through fiber element 215 that connects the heating assembly 220 with the fluid container 205. One or more apertures (not shown) allow the passage of the vapor that is produced when the fluid contacts the heated glass bulb 230.

The vapor then passes around the fluid container 205 and out through the end-cap aperture 82. The heating element 225 may be made of platinum wire, nickel chromium alloy or iron chromium aluminum alloy wire with a rare earth element. The tempered glass bulb 230 may also be manufactured from plastic, or other elements. One feature of this arrangement is that the fluid is not brought into direct contact with the heating element 225.

In one embodiment, the fiber element 215 comprises a high-temperature fiberglass fabric, but other materials may be employed, such as cotton, high-temperature conduction oil cotton, or other materials. Sealing material 210 located around the heating assembly 220 prevents any fluid from passing into the first chamber 20, and may also be constructed of a high-temperature fiberglass fabric, but other materials may be employed, such as cotton, high-temperature conduction oil cotton, or other materials.

An air pressure switch is located at a distal end of the first chamber 20 and may be mounted on, or separate from a printed circuit board 70. A light-emitting diode 75 (LED) is located adjacent to the printed circuit board 70, with the LED 75 forming an end-cap at one end of the electronic cigarette 200. A mouthpiece (not shown) may be located at the other end of the electronic cigarette 200, with the mouthpiece coupled to the end-cap 80 that includes a small aperture, or end-cap aperture 82 that allows passage of air from the second chamber 25 though the mouthpiece and into a user's mouth. The end-cap 80 may be made of silicone, plastic, metal or other materials.

The printed circuit board, or chip 70 in conjunction with the air pressure switch controls the function of the electronic cigarette 200. According to one embodiment, outside, or ambient air is drawn into the first chamber 20 through the air inlet (not shown). The air pressure switch senses the low pressure formed by a user "drawing" on the mouthpiece (not shown), and activates the heating element 225 by allowing electricity to flow from the battery to the heating element 225. The LED 75 also illuminates at this time. The air flows down the tube 55 and into the heating assembly 220, where the glass bulb 230 has atomized, or vaporized some of the fluid that is carried to the heating assembly 220 by the fiber element 215. The vaporized fluid mixes with the air, and passes though end-cap aperture 82.

As shown in FIG. 2, the printed circuit board, or chip 70 has three wires coupled to it, the anode wire 85, the cathode wire 90 and the air pressure switch wire 95. The anode wire 85 runs from the printed circuit board 70 to the anode side of the battery. The cathode wire 90 connects the printed circuit board 70 to the cathode side of the battery, and then passes through the first seal 50 and into tube 55 connecting to the heating assembly 220 by extending all the way through the tube 55. The air pressure switch wire 95 connects the air pressure switch to the heating assembly 220, by also passing through the first seal 50.

Figure 4:
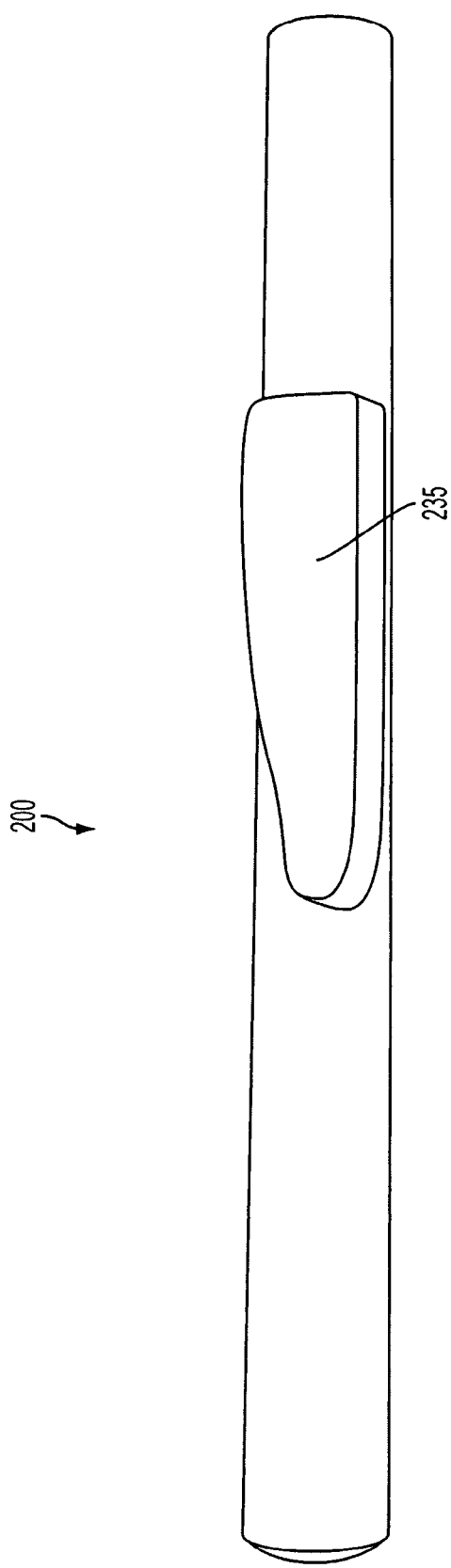
FIG. 4 is a view of an electronic cigarette showing a moveable clip feature.
Figure 5:
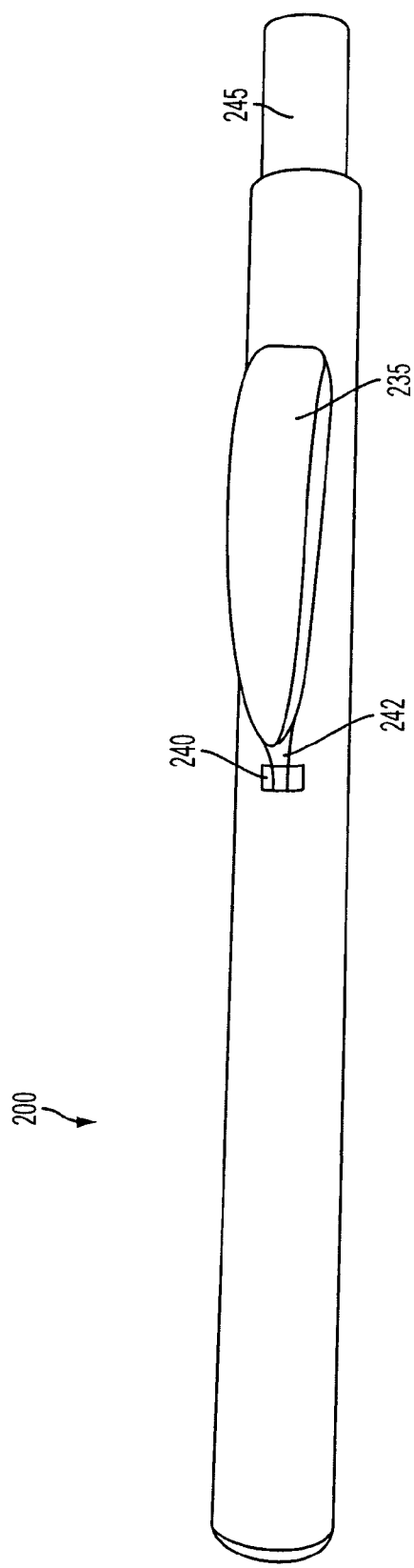
FIG. 5 is a view of an electronic cigarette showing a retractable tip feature.

Referring now to FIGS. 4 and 5, another feature of the electronic cigarette 200 is illustrated. Extendable tip 245 is retractable into the casing 15. As shown in FIG. 4, slideable clip 235, shaped substantially like a clip on a pen or the like, is slideable toward one end of the electronic cigarette 200. Rod, or connector 242 connects to the clip 235, with one end of the rod 242 slideably positioned in casing aperture 240.

As the clip 235 is moved toward the end of the electronic cigarette 200, extendable tip 245 extends from the casing 15. The extendable tip 245 may comprise a generally hollow member that a user would grasp with their lips to inhale the vapors exiting through end-cap aperture 82. The extendable tip 245 can be kept clean, and away from contaminants by being kept retracted within the casing 15 when the electronic cigarette 200 is not in use.

Also, the clip 235 may also be used to attach, or secure the electronic cigarette 200 to clothing, purses, pockets or other items. And, in one embodiment, the clip 235 may be shaped to act as a stand for the electronic cigarette 200. The "stand" may prevent direct contact of the extendable tip 245 to an unclean surface when the electronic cigarette 200 is placed on a surface.

An alternative embodiment extendable tip may comprise a rotatable piston (not shown) that includes threads that when rotated, the extendable tip rides upwardly or downwardly on the threads. To prevent the rotatable piston from merely turning in response to the motion of a driving member (not shown) so as not to slide, the interior wall may be provided with a guide member (not shown) that extends along at least a portion of the length of the rotatable piston and mates with a corresponding feature in the casing 15. In a preferred embodiment, the rotatable piston and the interior cross section may be given a shape that is other than circular. Preferably, the rotatable piston may have an oval or ellipsoid shape.

Figure 6:
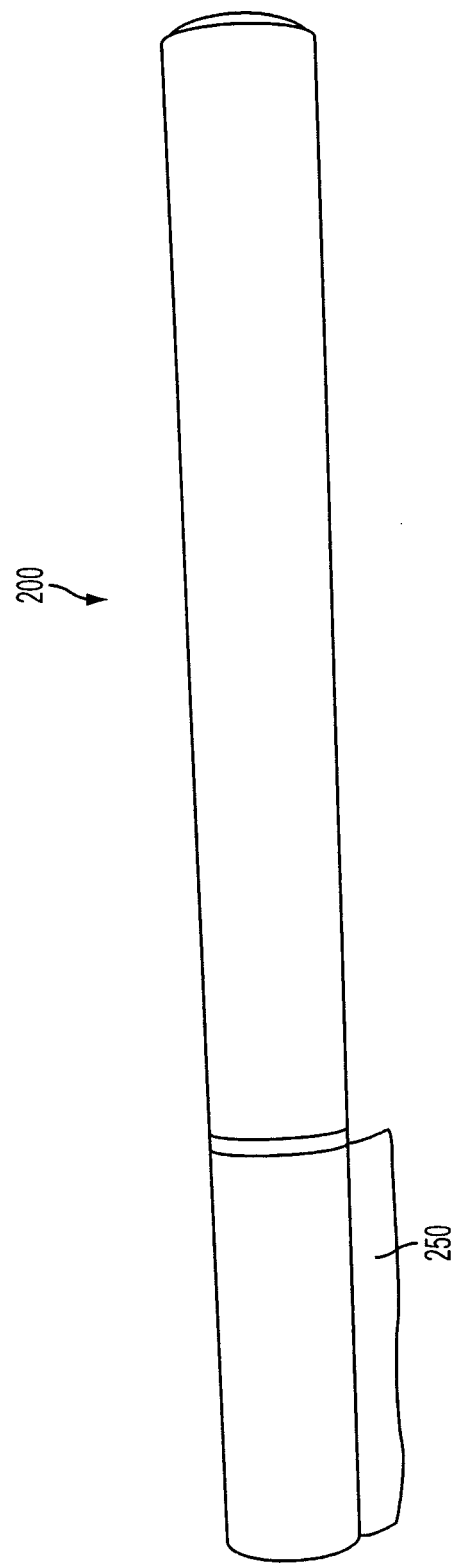
FIG. 6 is a view of an electronic cigarette showing a peel-away wrapper tip.
Figure 7:
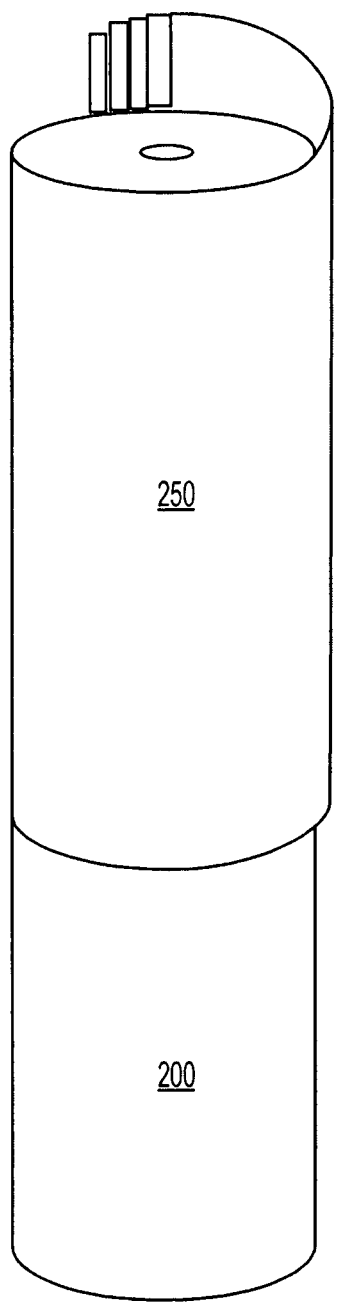
FIG. 7 is a view of the peel-away wrapper illustrated in FIG. 6.

Referring now to FIGS. 6 and 7, another feature of the electronic cigarette 200 is illustrated. Removeable wrapper 250 may be located at one distal end of the electronic cigarette 200, where a user would place their lips when drawing on the electronic cigarette 200. For example, in one embodiment, one or more sanitary peel-away wrappers 250 that can be removed as desired are coupled to the electronic cigarette 200, so that a user's lips are not exposed to a dirty or contaminated tip.

Figure 8:
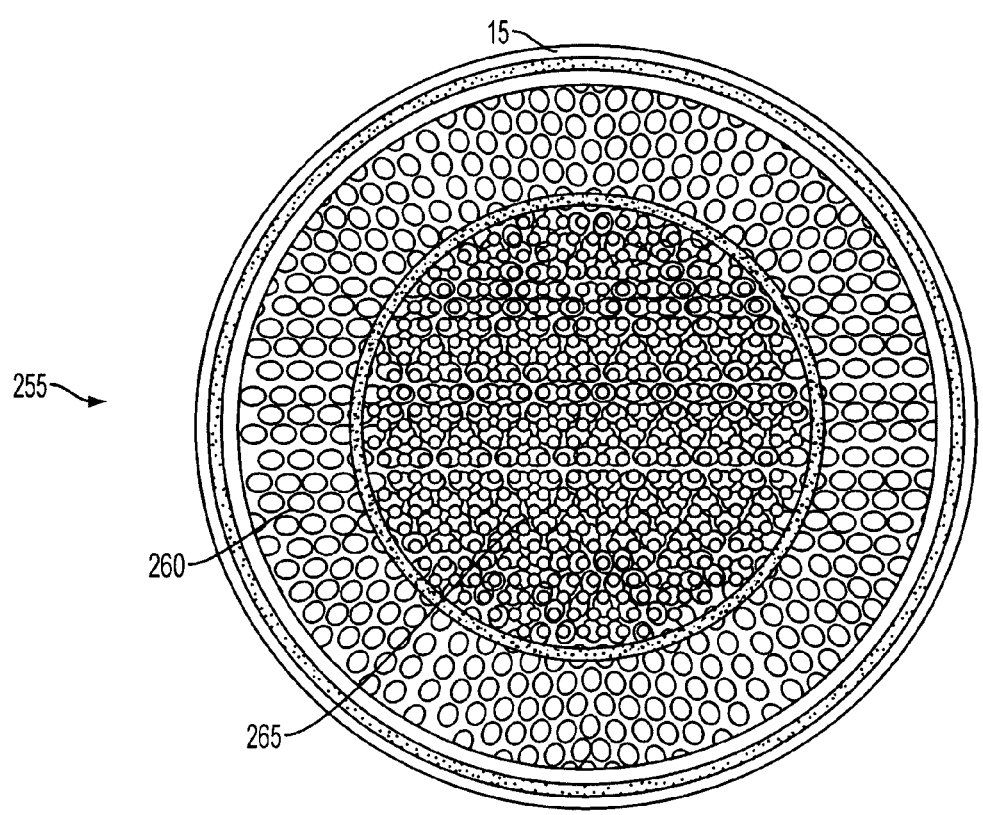
FIG. 8 is an end view of a filter element that may be included in a embodiment of an electronic cigarette.

Referring now to FIG. 8, another feature of the electronic cigarette 200 is illustrated. Some embodiments of the electronic cigarette 200 may include a filter assembly 255. The filter assembly 255 may be located at one distal end of the electronic cigarette 200, where a user would place their lips when drawing on the electronic cigarette 200. In one embodiment, the filter assembly 255 includes an inner element 265 and an outer element 260. One or both of the inner and outer elements 265 and 260 may be constructed of microfibers or other materials made of any polyester, polyamides, bamboo, wood or any cellulose fibers or any polymeric material that is capable of absorbing water or vapor, and that is capable of being impregnated with a flavor or chemical compound.

For example, one or both of the inner and outer elements 265 and 260 may comprise filtration and pass through structures comprise flow passages having a high surface area for contact with vapor passing there through, enabling the vapor to become enriched with nicotine, flavors, and other blends, either alone or in combination. In one arrangement, the outer element 260 may comprise a multiplicity of axially elongated fibrous filtering material members disposed concentrically to reduce the amount of water vapor carried into the lungs when inhaling vapors from the electronic cigarette 200.

In one embodiment, the inner element 265 comprises a section capable of dispensing volatile ingredients including nicotine, tobacco flavor, medications, and other flavoring. Reservoirs formed therein may be circular or noncircular in cross section. Absorbent material may be used to retain more volatiles within the section to better wick the volatile vapors when vapor or air is drawn through the electronic cigarette 200. Drawing vapor or air through the inner element 265 transfers vapors to the user. Loading of any material into the inner or outer elements 265 or 260 may be accomplished via sprayer, direct injection or a gaseous atmosphere conductive to preserving nicotine. The fluid mechanic principles of adhesion, cohesion capillary action and surface tension which can cause a thin film may be used. The basic properties, components and applications may be exchanged between the inner and outer elements 265 and 260.

Figure 9:
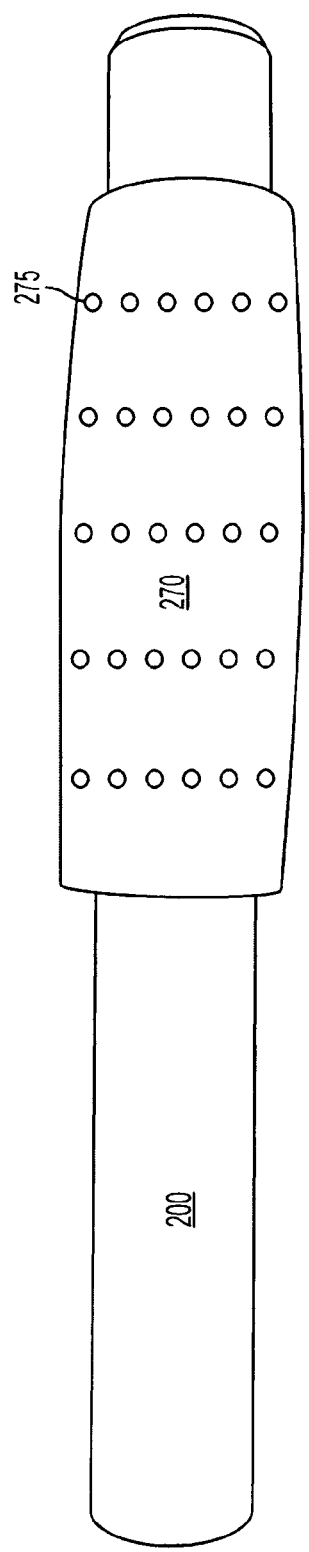
FIG. 9 is a view of a removeable sleeve that may be attachable to an electronic cigarette.

Now referring to FIG. 9, another feature of the electronic cigarette is illustrated. A removeable sleeve 270 may be placed over the casing 15 and positioned at any location along the casing 15. The removeable sleeve 270 includes a plurality of apertures 275 that may be filled with nicotine or other medications.

In one embodiment, the removeable sleeve 270 is constructed of rubber, latex, or a medical grade rubber, latex or plastic. During the manufacturing process, the plurality of apertures, or holes 275 are formed by a mold, or by other means. The plurality of apertures, or holes 275 may then be filled with any desired medication(s) (usually in a gel form) by immersing the removeable sleeve 270 in the medication or by injection. When injection is used no holes 275 need be added to the mold. In this embodiment, the removeable sleeve 270 is inserted into a device that injects the medications right into the sleeve material. After filling, a cellulite spray is applied to the removeable sleeve 270. The cellulite cover retains the medication in the holes 275 until the cellulite is broken when pressure is applied, thereby allowing the medications to provide transdermal drug delivery.

In another embodiment, a transdermal drug delivery system may be built into the cigarette itself without the use of the removeable sleeve 270. In this embodiment, an absorbent paper featuring a mesh overlay (not shown) may be employed. When manufactured, a paper is soaked with the desired medication. Then a mesh overly is applied which is made of medical grade rubber, latex or other material as described above in connection with the removeable sleeve 270. Next, the paper and mesh (not shown) are covered in a cellulite to seal the medication in. Then, the paper and mesh are wrapped around the desired product, which could be the electronic cigarette 200, or a cardboard tube that looks like a cigarette. When pressisure is applied to the paper the pressure removes the cellulite wrapper allowing finger tips to squeeze down the mesh and allow the medicated absorbent paper to provide a transdermal drug delivery.

In one embodiment, the electronic cigarette 200 is disposable. During operation, if a user smokes for more than 5 seconds per puff the LED flashes two times then shuts off, or will flash ten times, which indicates the battery 35 is running low on stored power.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

Thus, it is seen that electronic cigarette is provided. One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:
1. An electronic cigarette, comprising:
a casing comprising a first chamber and a second chamber, the two chambers located sequentially within the casing;
a battery located in the first chamber;
a fluid containing member located in the second chamber;
a heating assembly located in the second chamber, the heating assembly comprising a bulb containing a heating wire in communication with the battery;

a fluid passageway communicating between the fluid containing member and the heating assembly;

a tube element communicating between the first and second chambers, with a first distal end of the tube element located in the first chamber, and a second distal end of the tube element located in the second chamber and affixed to the bulb, the tube element providing an air passage between the first and second chambers;

a sealing element forming a partition between the first and second chambers; and an air inlet provided on an external wall of the casing;

wherein the heating wire heats the bulb, and wherein the bulb heats fluid introduced to and coming in contact with the bulb through the fluid passageway.

2. The electronic cigarette of claim 1, where the fluid passageway comprises a fiber element having a first distal end communicating with the fluid containing member, and a second distal end communicating with the heating assembly.

3. The electronic cigarette of claim 1, wherein said bulb comprises tempered glass.

4. The electronic cigarette of claim 1, further comprising a retractable tip member located at a distal end of the casing.

5. The electronic cigarette of claim 1, further comprising a filter apparatus located in a distal end of the casing.

6. The electronic cigarette of claim 1, further comprising a filter apparatus located in a distal end of the casing, the filter apparatus comprising two elements structured to allow the passage of air.

7. The electronic cigarette of claim 1, further comprising a removable sleeve positioned about a portion of an exterior of the casing.

8. The electronic cigarette of claim 1, further comprising a removable sleeve located around an exterior of the casing.

9. The electronic cigarette of claim 1, further comprising a removable sleeve located around an exterior of the casing, the removable sleeve comprising a plurality of apertures.

10. The electronic cigarette of claim 1, further comprising a removable sleeve located around an exterior of the casing, the removable sleeve comprising a plurality of apertures, the apertures capable of containing at least one medicament.

11. The electronic cigarette of claim 1, wherein the fluid is selected from a group consisting of: a glycol fluid, a fluid containing nicotine, a water-based "regular" cigarette flavored fluid, a water-based "menthol" cigarette flavored fluid, and combinations thereof.

12. An electronic cigarette, comprising:
a casing comprising a first chamber and a second chamber, the two chambers located sequentially within the casing;
a battery located in the first chamber;
a fluid containing member located in the second chamber;
a heating assembly located in the second chamber, the heating assembly comprising a bulb containing a heating wire in communication with the battery;
a fluid passageway communicating between the fluid containing member and the heating assembly;
a tube element communicating between the first and second chambers, with a first distal end of the tube element located in the first chamber, and a second distal end of the tube element located in the second chamber and affixed to the bulb, the tube element providing an air passage between the first and second chambers;
a sealing element forming a partition between the first and second chambers;
a printed circuit board located in the first chamber, the electronic circuit board communicating with an air pressure switch; and
a light-emitting diode (LED) coupled to a first distal end of the casing, the LED forming an end cap at the first distal end of the cylindrical casing and communicating with the printed circuit board; and
wherein the heating wire heats the bulb, and wherein the bulb heats fluid introduced to and coming in contact with the bulb through the fluid passageway.

13. The electronic cigarette of claim 12, further comprising a retractable tip member located at a distal end of the casing.

* * * * *